United States Patent [19]

Brinnand et al.

[11] Patent Number: 5,404,591

[45] Date of Patent: Apr. 11, 1995

[54] WRIST AND CARPAL PROTECTIVE GLOVE

[76] Inventors: Alfred Brinnand; Tana Brinnand, both of 75 Green Valley Rd., Scotts Valley, Calif. 95066

[21] Appl. No.: 268,720

[22] Filed: Jun. 20, 1994

Related U.S. Application Data

[63] Continuation of Ser. No. 723,781, Jul. 1, 1991, abandoned.

[51] Int. Cl.$^6$ ............................................. A41D 19/00
[52] U.S. Cl. ........................................... 2/20; 2/161.1; 2/161.6
[58] Field of Search ............. 2/16, 20, 161 R, 161 A, 2/239, 161.6, 162, 161.1, 159, 160, 161.7; 604/21

[56] References Cited

U.S. PATENT DOCUMENTS

| | | | |
|---|---|---|---|
| 309,892 | 12/1884 | Smith | 2/16 X |
| 403,783 | 5/1889 | Smart | 2/16 |
| 552,171 | 12/1895 | Farnham | 2/20 X |
| 1,280,158 | 10/1918 | Cardwell | 2/16 X |
| 1,351,378 | 8/1920 | Frankel | 2/16 X |
| 2,077,202 | 4/1937 | Barrie | 2/20 X |
| 3,501,773 | 3/1970 | Stansberry et al. | 273/166 X |
| 3,787,898 | 1/1974 | Walker | 2/163 |
| 4,519,097 | 5/1985 | Chappell, Jr. et al. | 2/161 A X |
| 4,520,635 | 6/1985 | Shields et al. | 2/239 X |
| 4,584,993 | 4/1986 | Nelson | 602/21 |
| 4,850,341 | 7/1989 | Fabry et al. | 602/21 |
| 5,081,715 | 1/1992 | Mascia | 2/20 |
| 5,150,475 | 9/1992 | Hansen et al. | 2/170 |
| 5,214,799 | 6/1993 | Fabry | 2/161.6 |
| 5,376,066 | 12/1994 | Phillips et al. | 2/16 |

FOREIGN PATENT DOCUMENTS

| | | | |
|---|---|---|---|
| 204305 | 4/1939 | Switzerland | 2/16 |
| 834027 | 5/1960 | United Kingdom | 2/168 |

Primary Examiner—Clifford D. Crowder
Assistant Examiner—Amy B. Yanatta
Attorney, Agent, or Firm—Paul F. Schenck

[57] ABSTRACT

The wrist and carpal protective glove includes a tubular section with padding enclosing the wrist region of an operator of control devices of computers or similar control equipment as protection against thermal and mechanical damage of the hand due to moving over a hard and cold desk surface. A thumb position which consists of flexible and stretchable material positions the padding relative to the thumb without restricting use of fingers and thumb during operation of the control device.

11 Claims, 9 Drawing Sheets

WRIST AND CARPAL PROTECTIVE GLOVE

This application is a continuation of application Ser. No. 07/723,781, filed on Jul. 1, 1991, now abandoned.

FIELD OF INVENTION

This invention relates to hand gloves, and more specifically to a wrist and carpal protective glove for users of a computer mouse, stylus, trackball, micro-fiche machine and similar apparatus which require sensitive manipulation by the fingers, and the resting and sliding of the wrist of the human hand on a hard worksurface; a glove that cushions and protects the skin and bones of the wrist and carpal area, yet allows the hand to slide smoothly over a worksurface, that does not interfere with the manipulation of delicate apparatus, and has an opening for the thumb to keep the wrist and carpal protective glove in place.

BACKGROUND

With the growing popularity of input devices such as the computer mouse, stylus, track-ball, micro-fiche machine and other electronic information processors, more and more people are spending extended periods of time involved with these instruments. All these activities entail that the weight of the hand rest mostly on the wrists, which in turn rests on or must slide over a hard, often cold, worksurface such as a table or graphics tablet. With extensive use, these activities cause the skin and bones of the wrist, particularly in the carpal region to become sore, abraded, and inflamed. Persistent pressure on this area causes annoyance, loss of concentration, discomfort, and may even damage the carpal nerve. The carpal nerve extends from the palm of the hand between the thumb and fourth finger into the top of the wrist, and damage to this nerve can lead to, or aggravate carpal tunnel syndrome. Moreover, in the case of children up to the ages of 13, these sensitive bones in the carpal area are not fully formed: they are still in the process of development. As such, children are in even greater need of protection than adults. This fact is particularly significant today as more and more primary and secondary schools are introducing students to the use of computers and their peripherals in the classrooms.

There have been various gloves and wrist protectors designed for sports and other activities, but none meets the particular requirements of the user of the above mentioned electronic input devices. Most versions of a wrist protective glove are in the areas of golf, bowling, and weight lifting. But as sports gloves they emphasize either a wrist brace to strengthen the wrist, as in weight lifting and bowling, or they include special padding for the palm area as in golf. Very often they involve braces to aid and develop a specialized kind of grip on sports apparatus.

DESCRIPTION OF PRIOR ART

A related entry in this field called "The Video Game Protective Glove" of CHAPPELL JR. et. al., S.N. 4,519,097 is concerned mainly with the palms and fingers of the wearer, but does not provide any wrist and carpal protection. The "Specialty Glove" of DEMARCO, S.N. 4,183,100 is concerned mainly with the grip, as in swinging an ax or baseball bat, or moving furniture. BERGER, S.N. 4,531,241 shows a hand glove suitable for operators of heavy equipment, rivet guns and jack-hammers, and pads the palm of the operators hand. DONALD CAMPANA's protective band, S.N. 4,896,378 is made of thick heavy neoprene which protects auto-mechanics against the accidental contact with sharp angled auto parts and hot metal surfaces.

None of the gloves in prior art is designed to protect the wrists of the human hand engaged in prolonged contact with a hard table-like worksurface which the use of a computer mouse, stylus or track-ball entails. The gloves of prior art do not provide protection to the skin and bones of the wrist and carpal area, without seriously limiting the flexibility and sensitivity needed to manipulate office and studio equipment. They do not offer an attractive light weight glove that is inexpensive, easy to put on and take off and will feel and look suitable in an office, class room or design studio environment.

DESCRIPTION OF THE FIGURES

FIG. 5b is an illustration of a cross section of the padded area taken from points v—v of FIG. 5a.

DESCRIPTION OF INVENTION

The wrist and carpal protective glove in this instance, is designed to protect the wrist and carpal region of the hand of people who are engaged in operating desk mounted machines such as computers, typewriters and micro-fiche machines. The glove consists of a glove body and a padded area at the wrist region. The glove body extends from the crotch between the thumb and the index finger, to just beyond the wrist region of the hand. The glove covers the heel of the palm, a portion of the back of the human hand, and has a hole for the thumb to extrude. The padding is attached to the glove body and is located directly between the wrist/carpus region and the worksurface on which the wrist rests. The padding provides thermal and mechanical protection to the wrist region while the wrist is involved in sliding or resting on the hard, potentially cold worksurface. Looping the glove body around the crotch between the thumb and the index finger prevents the padding from slipping up the forearm past the wrist region. Using a two way stretchable elastic material for the glove body such as "LYCRA ®", permits the glove to fit a wide range of hand sizes and shapes.

Several different methods of padding the glove are proposed as well as several methods of manufacturing the glove. One type of padding used in the preferred embodiment of the glove is constructed by attaching a piece of resilient vinyl-like material such as "NAUGAHYDE ®", over a similar sized piece of compressible material such as foam rubber, then stitching or gluing both pieces onto the glove body at the wrist region so that the vinyl is outermost, and will contact the worksurface, the glove body will contact with the operator's skin, and the compressible material between the glove body and the vinyl outer layer, cushions the operator's wrist. By extending the padded area all around the wrist so that the padding covers both the wrist region and the dorsal wrist region, the glove can be worn on either the right or left hand. The glove can be knitted in one piece, and the extra thickness for the padding achieved by changing the pattern in the wrist region. The glove can be made of one type of fabric or sheet material and the padding area established simply by folding the fabric or material back over the wrist region.

As this invention relates directly to the protection of the skin and bones of the wrist and carpal area of the human hand, to facilitate the description of the invention, the area of the glove body which covers the heel of the palm, the wrist and carpal bones on the palm side of the hand is referred to as the "wrist region of the glove body". The area of the human hand which consists of the heel of the palm, the wrist and carpal bones on the palm side of the hand is referred to as the "wrist region of the hand". The back or dorsal side of the wrist which faces away from the human body will be referred to as the "dorsal wrist region", as applied to the glove body or to the hand.

It is one object of the present invention to provide a device which effectively protects the user's carpal bones and the skin covering the wrist region of the hand from abrasion and damage due to prolonged pressure of the wrist on a hard table-like worksurface.

It is another object and advantage of this invention to provide an inexpensive, light weight flexible covering for the hand which leaves the fingers free for the sensitive requirements of manipulating a computer mouse, stylus, track-ball, or similar office equipment.

It is still another object to make a glove that stays in place, is easy to put on or take off and is suitable for a wide range of hand sizes.

It is still another object to provide a glove which is fashionably appropriate to an office, class room or design studio environment, and can be easily decorated or personalized.

It is still another object to provide a wrist protector which will in no way interfere with the user's manipulation of other office equipment, i.e., the wearer can as easily use it while entering data on a keyboard as handle a computer mouse.

It is still another object to provide a glove that absorbs excessive hand perspiration, minimize chafing, and will provide a comfortable, smooth contact between the user's wrist and the work surface.

Further benefits and advantages will become apparent from a consideration of the following detailed description given with reference to the accompanying drawings, which specify and show preferred embodiments of the invention.

DESCRIPTION OF THE PREFERRED EMBODIMENTS

Figure 1:
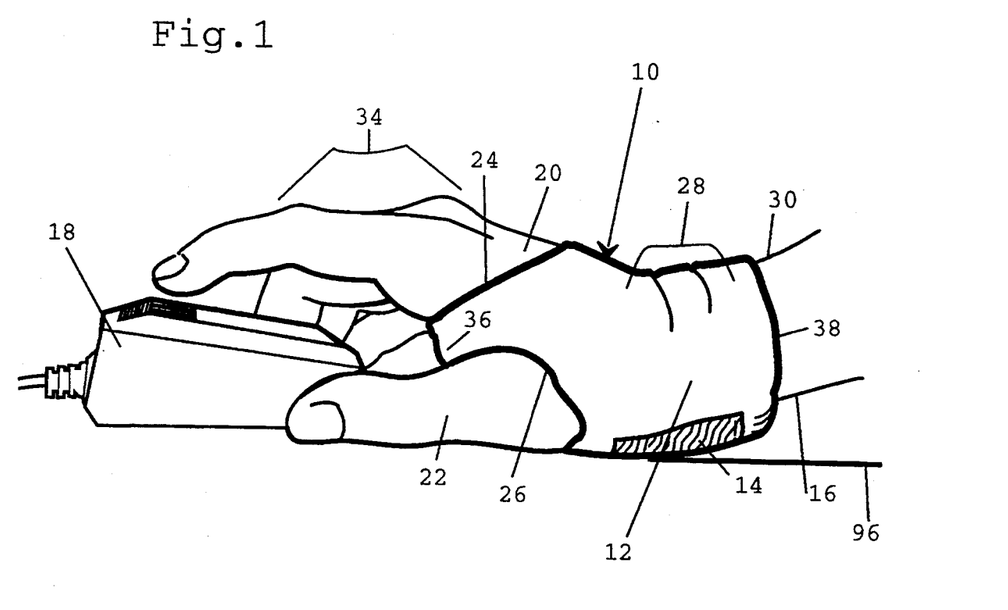
FIG. 1 is a side view of the glove on a hand operating a computer mouse.

Glove 10 as illustrated in FIG. 1, is composed of glove body 12 and wrist pad area 14. Glove 10 is generally tubular in construction and opens at three places allowing it to be slipped over fingers 34, thumb 22, and wrist 16 of the user. It extends from crotch 36 between thumb 22 and fingers 34, down to lower wrist 16, leaving thumb 22, and fingers 34 exposed. There is an opening 26 for thumb 22 to extrude. Crotch 36, holds glove 10 in place and prevents padded area 14 from slipping down over wrist 16. Padded area 14 is attached to glove body 12 to cover wrist region of hand 20. The purpose of padded area 14 is to cushion the user's carpal and wrist bones at the wrist region of hand 20, and protect the skin covering them from abrasions arising from prolonged contact with worksurface 96, which occurs while using computer mouse 18 or similar equipment. Glove 10 is designed to be snug yet allow for a wide range of different hand sizes and shapes. This can be accomplished by using a two way stretchable elastic material such as "LYCRA ®" for the construction of glove body 12.

Figure 2:
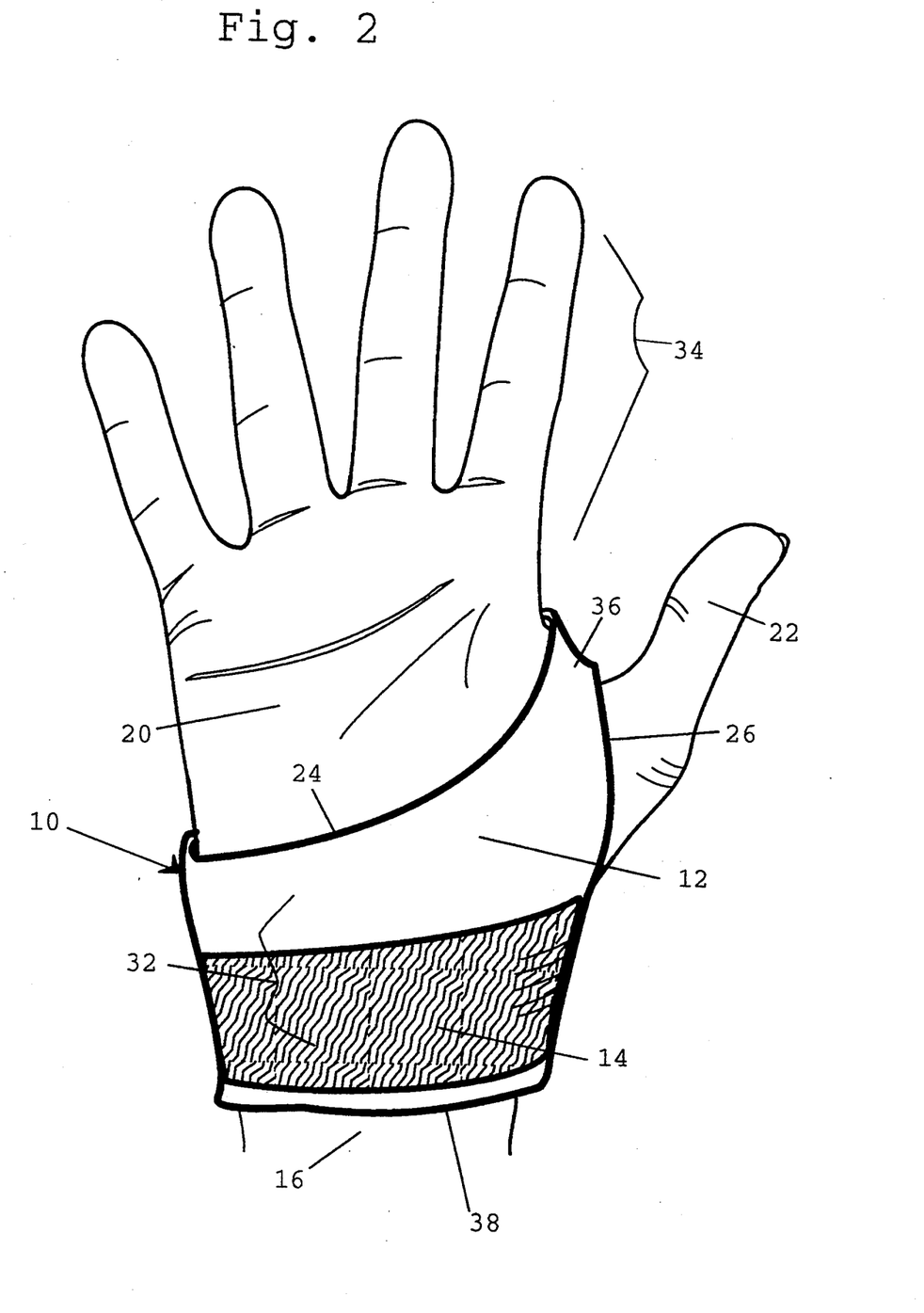
FIG. 2 is a view of the glove being worn on the right hand as seen from the palm side showing the padded area at the wrist region of the glove.
Figures 3, 4A:
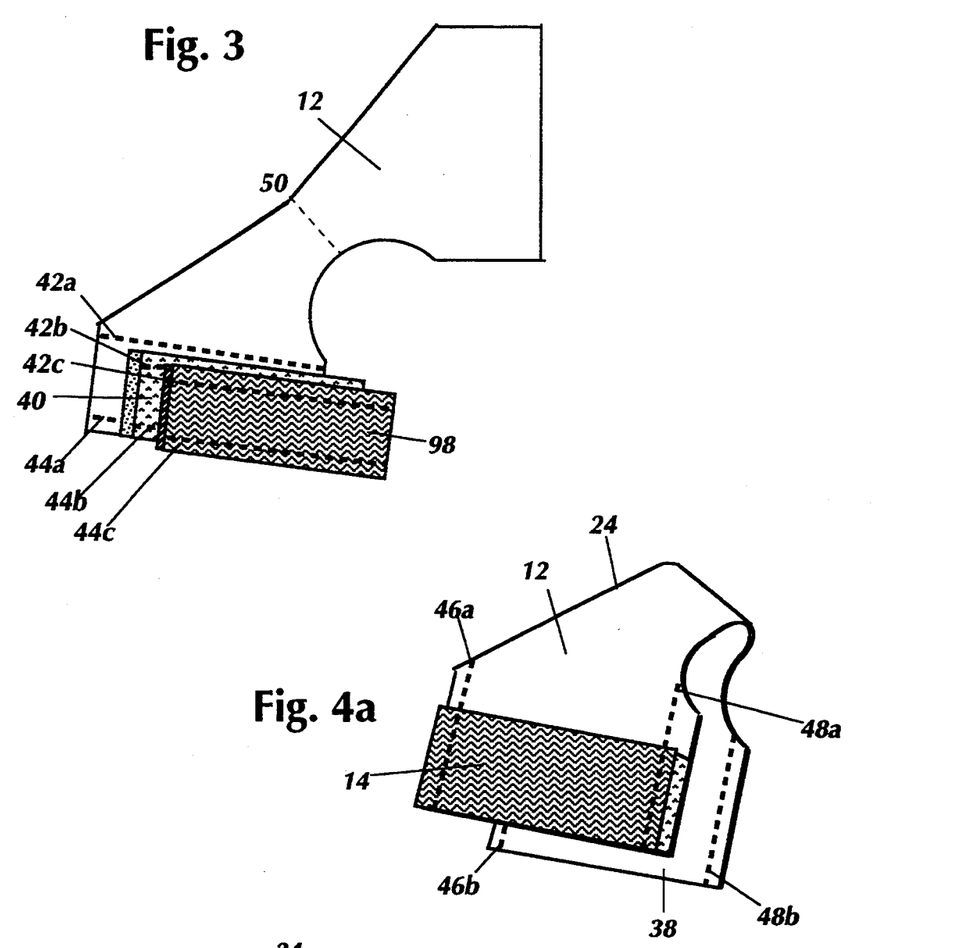
FIG. 3 Is an illustration of the material pattern of a preferred embodiment of the glove before assembly.
FIG. 4a is an illustration of the folded pattern of a preferred embodiment of the glove before joining.

Glove body 12 may be cut out of a single piece of material as shown in FIG. 3. In FIG. 3, lines 42a through 42c, and 44a through 44c represent the seam lines where compressible wrist pad 40 and wrist pad cover 98 are attached to glove body 12. The combination of wrist pad 40 and wrist pad cover 98 is one implementation of padded area 14 of FIG. 2. This implementation is described in more detail with reference to FIG. 9. Glove body 12 is folded along line 50 as seen in FIG. 3. In FIG. 4a, the folded halves are joined along lines 46a and 46b, and lines 48a and 48b. The completed glove (see also FIGS. 1, 2 and 5a), has opening 24 to slip over fingers 34 and the upper portion of hand 20, and has opening 26 for thumb 22, and opening 38 for wrist 16. In FIG. 4a, padded area 14 represents all implementations of padding discussed below.

Figure 4B:
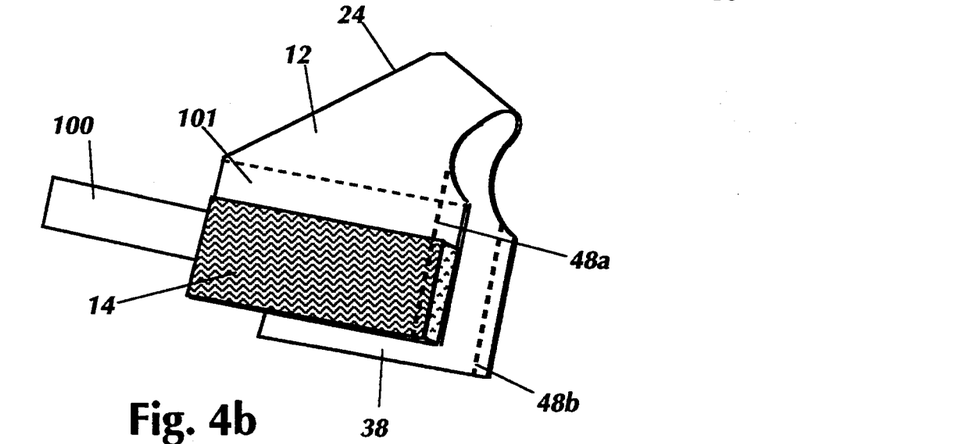
FIG. 4b is an illustration of a glove with an open wrist band and means for closing the wrist band.

FIG. 4b is a view of a glove in which wrist band 101 has a closing strip 100 attached. Closing strip 100 is preferably made with VELCRO" type material, and has a counter section attached to the dorsal wrist region of glove body 12. When attaching strip 100 to its counter section, wrist band 101 takes the function of a closed tubular section. It is understood that instead of VELCRO" like fastener, there are other kinds of fasteners such as hooks, laces, zippers and snaps that can be used as means for closing the glove which fall within the true spirit of the invention.

Figure 5A:
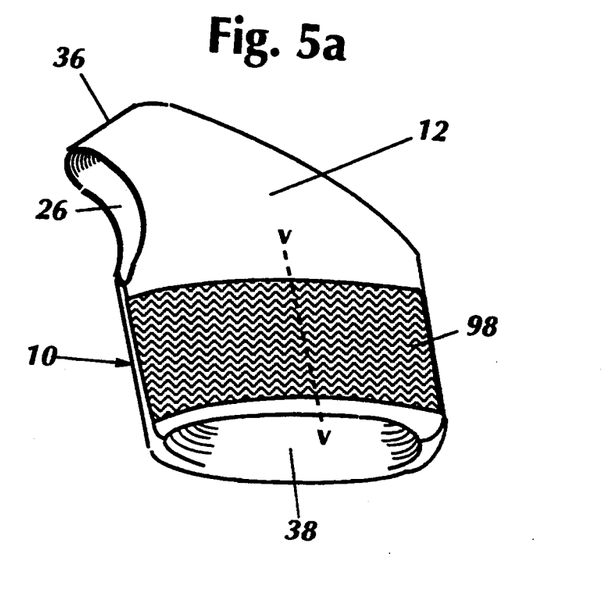
FIG. 5a is an illustration of a completed preferred embodiment of the glove with hidden seams.
Figure 5B:
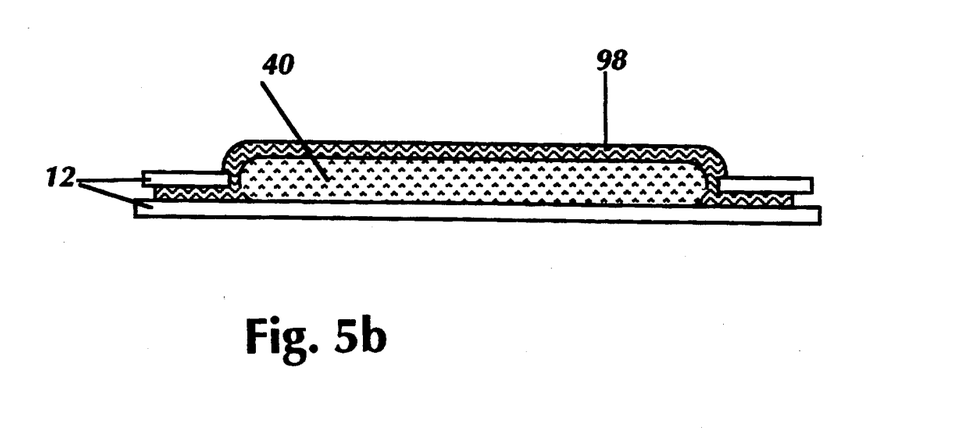

FIG. 5b is a cross sectional view of the padding taken between points v—v of FIG. 5a.

The surface of glove 10 that contacts the skin is referred to as the inside surface of glove 10 and the surface that faces away from the skin is referred to as the outside surface of glove 10.

A wide range of natural and synthetic materials well known to those skilled in the art, which are flexible, elastic, washable, breathable and retain their shape may be used to make the body of the glove. Moreover, there are also a variety of resilient, flexible, soft, elastic and washable materials that can be used to make the pad for the wrist region of glove 10. Additionally it is noted that padded area 14, see FIGS. 1 and 2, can be constructed and attached to a glove body in a variety of ways.

In FIGS. 6, 7, 8, and 9, different ways to attach padding material to the wrist region of the glove body are illustrated.

Figure 6:
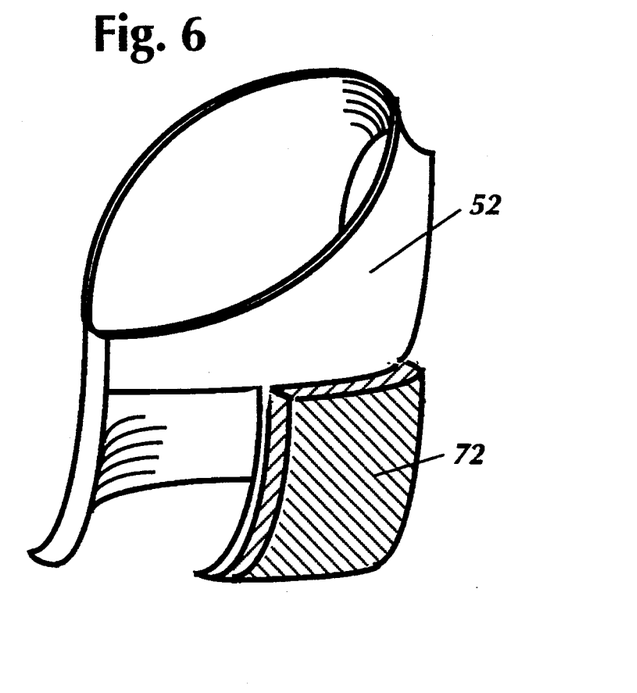
FIG. 6 is a cut-away view of the wrist region of a glove body showing a padded material added to the outer surface of the wrist region of the glove body.

In FIG. 6, padding 72 is attached to the outside of glove body 52.

Figure 7:
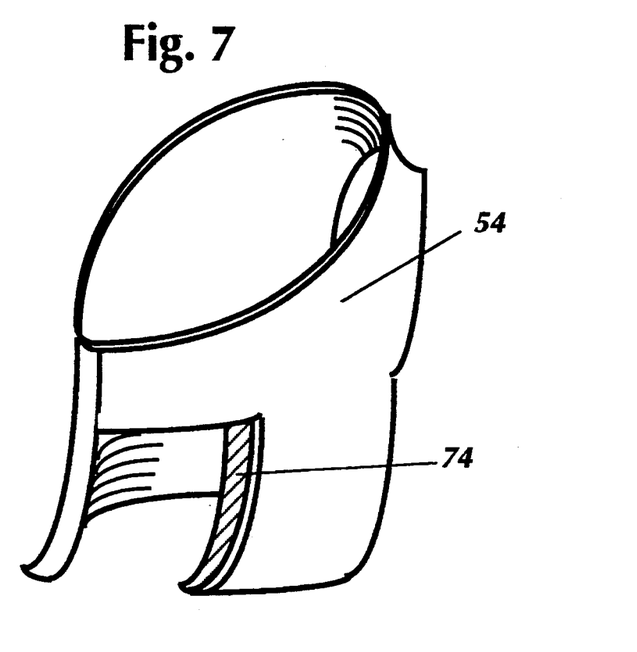
FIG. 7 is a cut-away view of the wrist region of a second glove body having a layer of padding added to the inner surface of the wrist region of the glove body.

In FIG. 7, padding 74 is attached to the inside of glove body 54.

Figure 8:
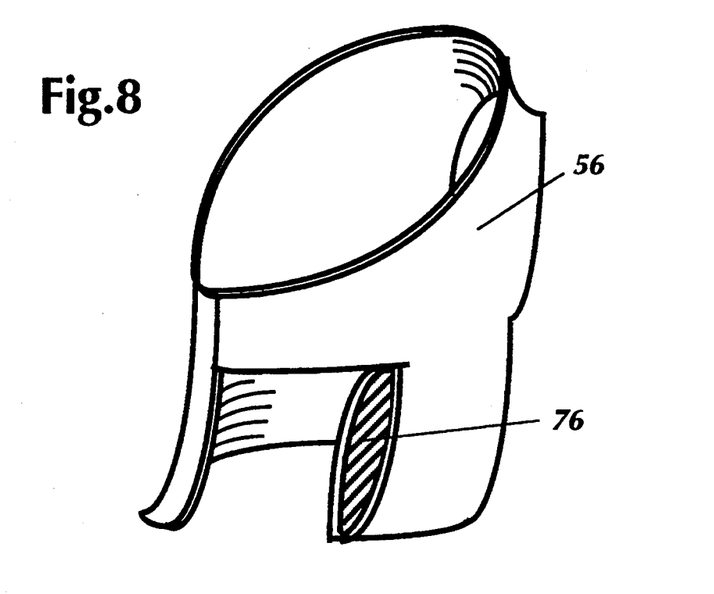
FIG. 8 is a cut-away view of the wrist region of a third glove body having a pad embedded between the inner and outer layers of the glove body at the wrist region of the glove body.

In FIG. 8, padding 76 is embedded between two layers of glove body 56. Padding 76, may be injected into the wrist region of the glove, as with silicone, or may consist of a variety of substances including plastic encased air sacs, and other soft compressible or deformable materials.

Figure 9:
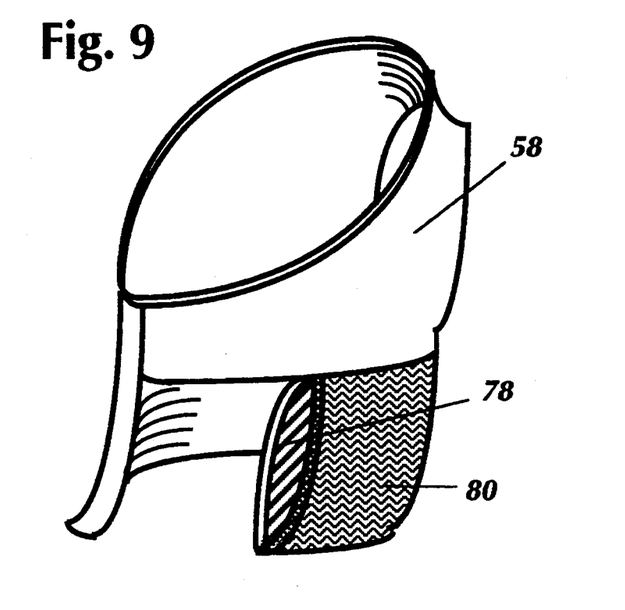
FIG. 9 is a cut-away view of the wrist region of a fourth glove body having a pad embedded between the glove body and a protective outer layer secured to the outer surface of the wrist region of the glove body.

In FIG. 9, padding 78 is sandwiched between material of glove body 58 and padding cover 80. Both padding 78 and padding cover 80 are secured to the outside wrist region of glove body 58. Padding cover 80 may consist of any smooth, flexible, resilient material.

Figure 10:
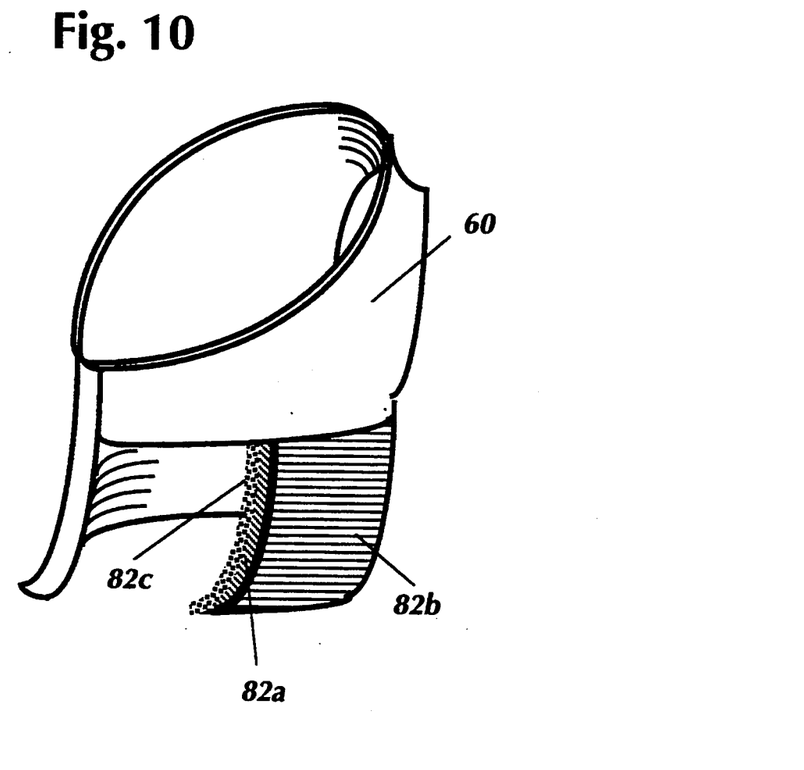
FIG. 10 is a view of a cut-away section of the wrist region of a fifth glove body having a pad replacing the glove body at the wrist region of the glove body.

In FIG. 10, padding 82a replaces wrist region of glove body 60, in such a way that the padding material is in direct contact with the skin of the wrist region of the user's hand, and consists of material that has an inner surface 82c with the quality of polypropeline to wick away perspiration, and an outer surface 82b with the quality of a smooth polymer or closed cell elastomer so that dirt lying on the worksurface will not be easily picked up.

FIGS. 11 to 14 are illustrations of gloves where the padding material encloses both the wrist region and the dorsal wrist region of the glove body, allowing the glove to be worn on either the right or left hand.

Figure 11:
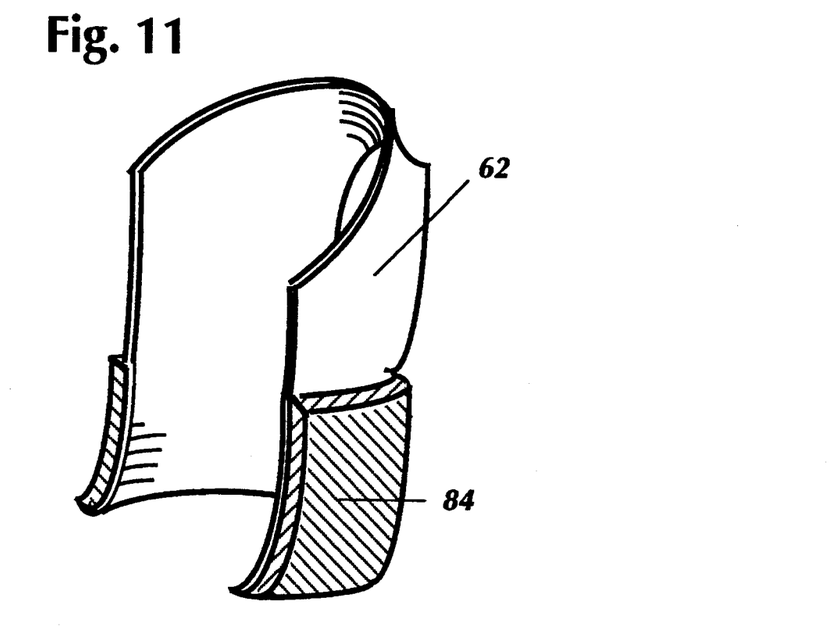
FIG. 11 is a cut-away view of the wrist region of a sixth glove body having a layer of padding added to the outer surface of the wrist region and dorsal wrist region of the glove body.

In FIG. 11, padding 84 is attached to the outside of glove body 62.

Figure 12:
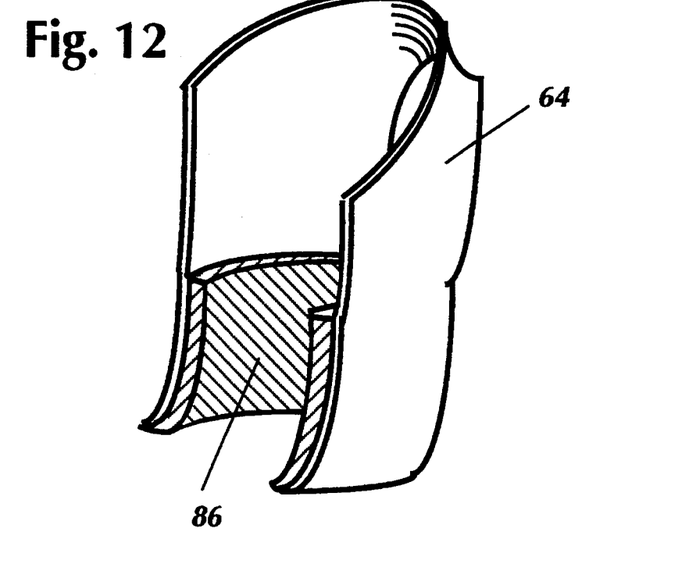
FIG. 12 is a cut-away view of the wrist region of a seventh glove body having a layer of padding added to the inner surface of the wrist region and the dorsal wrist region of the glove body.

In FIG. 12, padding 86 is attached to the inside of glove body 64.

Figure 13:
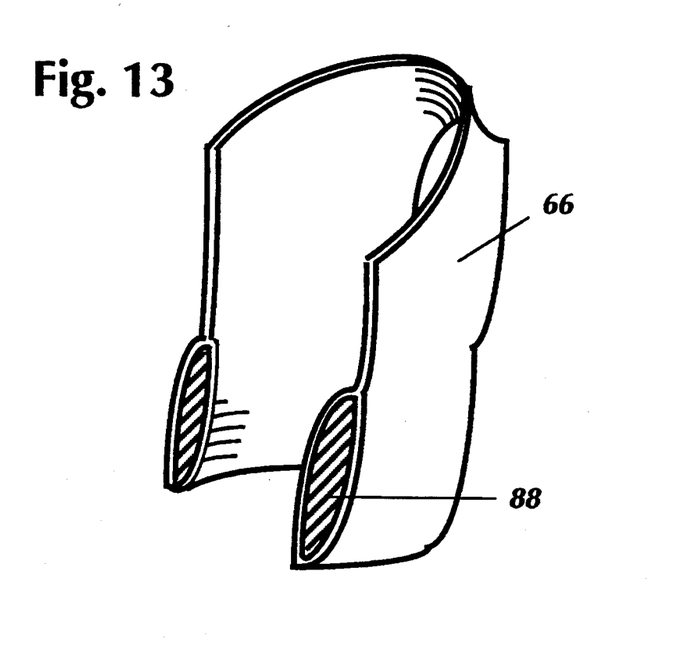
FIG. 13 is a view of a cut away section of an eighth glove body having a padded layer embedded between two layers of the glove body, the padded layer covering the wrist region and the dorsal wrist region of the glove body.

In FIG. 13, padding 88 is embedded between two layers of glove body 66.

Figure 14:
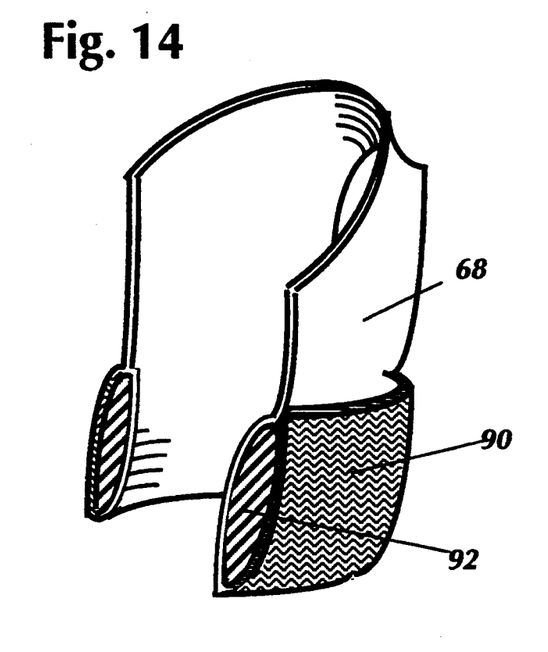
FIG. 14 is a view of a cut away section of a ninth glove body having an outer layer of material covering an inner padded layer, and both layers secured to the outer surface of the glove body in such a way that the two layers cover the wrist region and the dorsal wrist region of the glove body.

In FIG. 14, padding 92 and pad cover 90 are attached to the outside of glove body 68.

Figure 15:
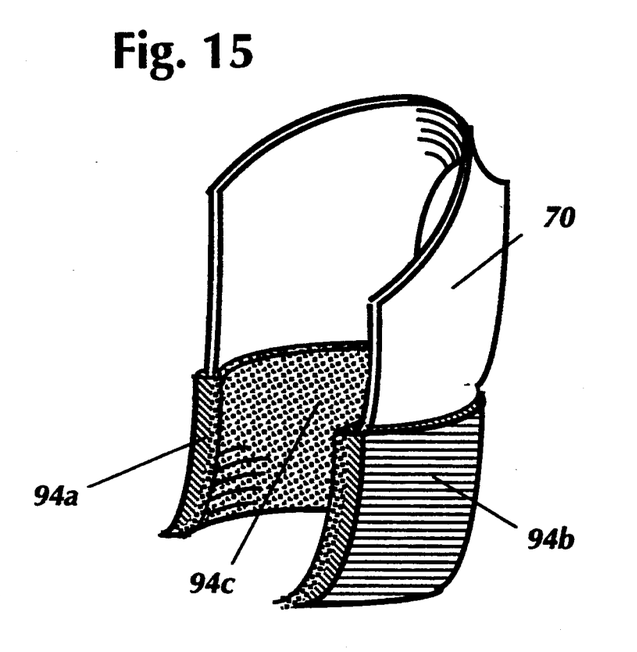
FIG. 15 is a view of a cut-away section of a tenth glove body having a layer of padding replacing the glove body at the wrist region, and that the padding encircles both the wrist region and the dorsal wrist region of the hand.

In FIG. 15, the glove body 70 extends only to the lower palm area, but does not cover the wrist region or dorsal wrist region of the hand: only the padding material attached to glove body 70 covers the wrist region and dorsal wrist region of the hand, and comes in direct contact with the skin of the wrist region and dorsal wrist region of the hand. Padding 94a may consist of material that has an inner surface 94c with the quality of polypropeline, to wick away perspiration, and an outer surface 94b with the quality of a smooth polymer or closed cell elastomer so that dirt lying on the worksurface will not be easily picked up.

Instead of using a glove body and attaching padding material to it, the glove may be formed of one piece of compressible elastic material such as neoprene or a similar elastomer with a thicker area serving as a pad in the wrist region. The padded region may also be formed out of two or more layers of elastomer laminated to form a softer pad on the inner side of the wrist region of the glove body and a tougher more resilient surface on the outside of the wrist region of the glove body.

It is apparent that the glove can be personalized in many ways such as by attaching metal studs or beads to the outer surface of the glove body, or by printing, embroidering, stenciling names, logos or colorful designs onto the glove body. The glove can be adapted to hold a watch or ornaments of plastic or metal. It is intended that the claims herein appended will cover all such modifications and embodiments as fall within the true spirit and scope of the present invention.

What we claim is:

1. A wrist protecting glove for a hand of an operator of control devices of electronic equipment, said control devices being mounted on a support surface, said glove supporting the wrist region and protecting the wrist region of said operator's hand from damage due to contact with the support surface, said glove comprising a tubular section surrounding the wrist of said operator's hand and having a first area protecting said wrist region of said hand facing the support surface and a second area covering the dorsal wrist region of said hand, and a thumb position section extending from said tubular section and covering at least the heel area and the ball of the thumb area of said operator's hand, providing a first opening for the thumb and a second undivided opening diagonally reaching across said operator's hand between the heel of the palm and the crotch between the thumb and the index finger;

said thumb position section including flexible material being stretchable in two dimensions for adaptation of said thumb position section to said operator's hand, said thumb position section providing unlimited movement of said hand and proper positioning of said first area relative to said wrist area;

said first area including flexible padding for thermal and mechanical protection of said operator's wrist region, said padding extending at least partially around said wrist region laterally from the heel area to the ball area of said hand across the center of the wrist, said padding having an outer surface adapted for easy sliding on said support surface of said control devices.

2. A wrist protecting glove for a hand of an operator of control devices of electronic equipment, said control devices being mounted on a support surface, said glove supporting the wrist region, and protecting the wrist region of said operator's hand from damage due to contact with the support surface without limiting the movement of the fingers and the thumb of the hand, said glove comprising a tubular section surrounding the wrist of said operator's hand and having a first area covering said wrist region opposing said surface, said first area of said tubular section being made of padding material for thermal and mechanical protection of said wrist region, and a second area covering the dorsal wrist region of said hand, said first area extending at least partially around said wrist region laterally from the heel area to the ball area of said hand across the center of the wrist, said padding material having an outer surface adapted for easy sliding on said support surface of said control devices; and a thumb position section extending from said tubular section, covering at least the heel area and the ball of the thumb area of the hand of said operator and providing a first opening for the thumb of said operator and a second undivided opening diagonally reaching across said operator's hand between the heel of the palm and the crotch between the thumb and the index finger;

said thumb position section including flexible material being stretchable in two dimensions for adaptation of said thumb position section to said operator's hand, thereby providing unlimited movement of said hand and proper positioning of said first area relative to said wrist area.

3. A wrist glove as claimed in claim 2, wherein said second area of said tubular section is also being made of padding material.

4. A wrist glove as claimed in claim 2, wherein said padding material has a resilient outer surface and an elastic core section.

5. A wrist glove as claimed in claim 3, wherein said padding material has a resilient outer surface and an elastic core section.

6. A wrist protecting glove for a hand of an operator of control devices of electronic equipment, said control devices being mounted on a support surface, said glove supporting the wrist region and protecting the wrist region of said operator's hand from damage due to contact with the support surface, without limiting the movement of the fingers and the thumb of the hand, said glove comprising a tubular section surrounding the wrist of said operator's hand and having a first area protecting said wrist region and facing said support surface, and a second area covering the dorsal wrist region, and a thumb position section extending from said tubular section and covering at least the heel area and the ball of the thumb area of said operator's hand, providing a first opening for the thumb and an undivided second opening diagonally reaching across said operator's hand between the heel of the palm and the crotch between the thumb and the index finger;

said first area including padding for thermal and mechanical protection of said operator's wrist region facing said support surface, said padding extending at least partially around said wrist region laterally from the heel area to the ball area of said hand across the center of the wrist, said padding material having an outer surface adapted for easy sliding on said support surface of said control devices; and wherein said tubular section is made from stretchable elastic material to adapt to different wrist sizes;

said thumb position section including flexible material being stretchable in two dimensions for adaptation of said thumb position section to said operator's hand, thereby providing unlimited movement of said hand and proper positioning of said first area relative to said wrist area.

7. A wrist protecting glove for a hand of an operator of control devices of electronic equipment, said control devices being mounted on a support surface, said glove supporting the wrist region and protecting the wrist region of said operator from damage due to contact with the support surface without limiting the movement of the fingers and the thumb of the hand, said glove comprising a wrist band section for forming a tubular section surrounding the wrist of said operator's hand and having a first and a second end and closing means for attaching said first end to said second end, said wrist band forming a tubular section when wrapped around said operator's wrist and closed by said closing means, said so formed tubular section having a first area protecting said wrist region facing said support surface, and a second area covering the dorsal wrist region; and a thumb position section extending from said tubular section and covering at least the heel area and the ball of the thumb area of said operator's hand, providing a first opening for the thumb and a second, undivided opening diagonally reaching across said operator's hand between the heel of the palm and the crotch between the thumb and the index finger;

said first area including padding for thermal and mechanical protection of said operator's wrist region said padding extending at least partially around said wrist region laterally from the heel area to the ball area of said hand across the center of the wrist, said padding material having an outer surface adapted for easy sliding on said support surface of said control devices; and said thumb position section including flexible material being stretchable in two dimensions for adaptation of said thumb position section to said operator's hand, thereby providing unlimited movement of said hand and proper positioning of said first area relative to said wrist area.

8. A wrist protecting glove as claimed in claim 1, 6, or 7 wherein said second area of said tubular section also includes padding for thermal and mechanical protection of said operator's wrist region said padding thereby extending fully around said wrist region.

9. A wrist glove as claimed in claim 1, 6, or 7, wherein said tubular section has an inner layer and an outer layer and wherein said padding is placed between said inner layer and said outer layer.

10. A wrist protecting glove as claimed in claim 7, wherein said first end and said second end include means for attaching said first end to said second end upon pressing said first end on said second end.

11. A wrist glove as claimed in claims 2, 3, 4 or 5, wherein said tubular section includes an outside surface facing said surface of said table, and an inside surface facing said operator's wrist region, and wherein said padding material consists of material with a non-uniform density distribution between the outside surface and the inside surface, said padding material having a high density at said outside surface and a low density at said inside surface.

* * * * *